United States Patent [19]

Braren et al.

[11] Patent Number: 4,925,523
[45] Date of Patent: May 15, 1990

[54] ENHANCEMENT OF ULTRAVIOLET LASER ABLATION AND ETCHING ORGANIC SOLIDS

[75] Inventors: Bodil E. Braren, Hartsdale; Rangaswamy Srinivasan, Yorktown Heights, both of N.Y.

[73] Assignee: International Business Machines Corporation, Armonk, N.Y.

[21] Appl. No.: 380,787

[22] Filed: Jul. 17, 1989

Related U.S. Application Data

[63] Continuation of Ser. No. 264,476, Oct. 28, 1988, abandoned.

[51] Int. Cl.$^5$ .................. B44C 1/22; B29C 37/00
[52] U.S. Cl. ................................ 156/643; 156/651; 156/654; 156/668; 219/121.69; 219/121.76
[58] Field of Search .............. 250/492.1, 492.2, 492.3, 250/494.1, 503.1, 504 R; 156/643, 651, 654, 655, 659.1, 668; 219/121.67, 121.68, 121.69, 121.74, 121.75, 121.76, 121.77; 427/53.1

[56] References Cited

U.S. PATENT DOCUMENTS

| | | | |
|---|---|---|---|
| 3,622,742 | 11/1971 | Cohen et al. | 219/121.6 |
| 3,710,798 | 1/1973 | Bredemeier | 128/303.1 |
| 4,054,094 | 10/1977 | Caddell et al. | 101/467 |
| 4,289,378 | 9/1981 | Remy et al. | 350/174 |
| 4,408,602 | 10/1983 | Nakijima | 128/303.1 |
| 4,414,059 | 11/1983 | Blum et al. | 156/659.1 |
| 4,417,948 | 11/1983 | Mayne-Banton et al. | 156/643 |
| 4,440,801 | 4/1984 | Aviram et al. | 427/54.1 |
| 4,451,503 | 5/1984 | Blum et al. | 427/53.1 |
| 4,508,749 | 4/1985 | Brannon et al. | 427/43.1 |
| 4,568,632 | 2/1986 | Blum et al. | 430/322 |
| 4,627,436 | 12/1986 | Leckrone | 128/303.1 |
| 4,687,539 | 8/1987 | Burns et al. | 156/626 |
| 4,701,591 | 10/1987 | Masaki et al. | 219/121.76 X |
| 4,715,318 | 12/1987 | Kameyama et al. | 219/121.77 X |
| 4,749,840 | 6/1988 | Piwczyk | 219/121.69 X |
| 4,784,135 | 11/1988 | Blum et al. | 128/303.1 |

OTHER PUBLICATIONS

D. L. Klein et al., "Ablative Photocomposition Process for Repair of Line Shorts," IBM Technical Disclosure Bulletin, vol. 26, No. 9 (2/84), p. 4669.

R. Srinivasan et al., "Mechanism of the Ultraviolet Laser Ablation of Polymethyl Methacrylate at 193 and 248 nm: Laser-Induced Fluorescence Analysis Chemical Analysis, and Doping Studies", J. Opt. Soc. Am.B-/vol. 3, No. 5 (5/86), p. 785.

R. Srinivasan et al., "Ablative Photodecomposition of Polymer Films by Pulsed Far-Ultraviolet (193 nm) Laser Radiation: Dependence of Etch Depth on Experimental Conditions," J. Pol. Science, vol. 22, p. 2601 (1984).

B. J. Garrison et al., "Laser Ablation of Organic Polymers: Microscopic Models for Photochemical and Thermal Processes," J. Appl. Phys., 57 (8), p. 2909 (4/15/85).

J. T. C. Yeh, "Laser Ablation of Polymers," J. Vac. Sci. Technol. A 4 (3), p. 653 (May/Jun. 1986).

R. Srinivasan et al., "Photochemical Cleavage of a Polymeric Solid: Details of the Ultraviolet Laser Ablation of Poly(Methyl Methacrylate) at 193 and 248 nm," Macromolecules, vol. 19, p. 916 (1986).

(List continued on next page.)

Primary Examiner—William A. Powell
Attorney, Agent, or Firm—Bernard E. Shay

[57] ABSTRACT

A method and apparatus are described which enhance the ablative effect of a UV laser. The ablative effect of a pulsed UV laser is enhanced using a second, longer wavelength pulsed laser. Each pulse of the first laser is followed by or combined with a pulse from the second laser. The etch depth per pulse is controlled by varying the time between pulses from the first and second lasers. The maximum etch depth per pulse occurs at a time separation which is a function of the substrate being etched. The first laser wavelength is selected to be within the absorption spectrum of the unexcited surface molecules of the substrate, while the wavelength of the second laser is selected to be within the absorption spectrum of the surface molecules excited by the incident radiation of the first laser.

30 Claims, 6 Drawing Sheets

U.S. PATENT DOCUMENTS

B. Braren et al., "Optical and Photochemical Factors which Influence Etching of Polymers by Ablative Photodecomposition," J. Vac. Sci. Technol. B 3 (3), p. 913 (May/Jun. 1985).

G. Koren, "$CO_2$ Laser Assisted UV Ablative Photoetching of Kapton Films," Appl. Phys. Lett., vol. 45, No. 1, Jul. 1984, pp. 10–12.

M. Stuke & R. Larciprete, "Direct Observation of Excimer Laser Photoablation Products by Picosecond-UV-Laser Mass Spectroscopy," Applied Physics, Mar. 1986, pp. 57–58.

R. Srinivasan and V. Mayne-Banton, "Self-Developing Photoetching of Poly (Ethylene Terephthalate) Films by Far-Ultraviolet Excimer Laser Radiation," Appl. Phys. Lett. 41 (6), pp. 576–578 (9/15/82).

R. Srinivasan and W. J. Leigh, "Ablative Photodecomposition: Action of Far-Ultraviolet (193 nm) Laser Radiation on Poly (Ethylene Terephthalate) Films," Journal of the American Chemical Society, 104, 6784 (1982).

G. Koren and J. T. C. Yeh, "Emission Spectra, Surface Quality, and Mechanism of Excimer Laser Etching of Polyimide Films," Appl. Phys. Lett., 44 (12), pp. 1112–1114 (6/15/84).

G. Koren and J. T. C. Yeh, "Emission Spectra and Etching of Polymers and Graphite Irradiated by Excimer Lasers," J. Appl. Phys., 56 (7), pp. 2120–2126 (10/1/84).

J. E. Andrew, P. E. Dyer, D. Forster and P. H. Key, "Direct Etching of Polymeric Materials Using a XeCl Laser," Appl. Phys. Lett., 43 (8), pp. 717–719 (10/15/83).

E. Sutcliffe and R. Srinivasan, "Dynamics of UV Laser Ablation of Organic Polymer Surfaces," J. Appl. Phys., 60 (9), pp. 3315–3322 (11/1/86).

R. Srinivasan, E. Sutcliffe and B. Braren, "Analysis of the Dynamics of the Interaction of Ultraviolet Lasers with Organic Polymers," Laser Chem., vol. 9, pp. 147–154 (1988).

Fig. 1

PMMA at 193nm + 308nm

Schematic Diagram
of Experiment

Fig.6

ENHANCEMENT OF ULTRAVIOLET LASER ABLATION AND ETCHING ORGANIC SOLIDS

This is a continuation of application Ser. No. 264,476, filed Oct. 28, 1988, now abandoned.

The present invention relates in general to the ablation of organic polymers and biological tissue and more particularly to an improved ablation technique wherein pulsed lasers at a first and second wavelength are used simultaneously or in time correlation.

BACKGROUND OF THE INVENTION

The use of radiation from lasers in medical and dental procedures has been known for some time, having been applied shortly after the invention of the laser. In early work, which used infrared or visible lasers, medical researchers treated animal and human retinas and showed that the laser beam could induce a lesion on the retina for therapeutic purposes. Such laser eye surgery using visible or infrared lasers for detached retinas and other disorders is now routine in eye clinics throughout the world. In these medical applications, and in other applications using laser beams, the laser beam is absorbed by the irradiated tissue causing heating, denaturing of protein, and tissue death. The results are therapeutic because of the formation of scar tissue, cauterization of blood vessels, or the cutting away of diseased or damaged tissue.

Thus, in the early prior art, lasers were used to provide a directed source of radiation whose thermal energy led to the pyrolysis of the organic matter. However, there are many situations where heating is not desired and is, in fact, harmful; in those situations such lasers may not be used. For example, infrared lasers, which cut by heating a material substrate rather than by photochemical ablation, are normally not desirable for etching polymers and other organic materials (such as biological layers) since the region which is heated cannot be adequately controlled, especially for deep cuts. As will be more apparent from the following, the present invention is directed to a technique and apparatus for etching in a manner which avoids unnecessary heating damage to the substrate. In 1982 it was first reported that ultraviolet radiation of less than 200 nm-wavelength has a very high efficiency for decomposing polymers and organic biological matter by electronic excitation of the constituent bonds of the organic matter, followed by bond breaking. This phenomenon is referred to as ablative photodecomposition (APD). The irradiated material is removed by a ablative photodecomposition without substantially heating or otherwise damaging the remaining material. This is a relatively linear photochemical effect, and inhomogenities in the organic materials do not affect the photo etching. This phenomenon was subsequently found to extend to longer ultraviolet wavelengths. Currently, UV lasers of wavelengths from 193 nm to 351 nm are used in polymer ablation as well as in surgery on the cornea and angioplasty.

Ultraviolet radiation is defined as including wavelengths between 150 and 400 nm. In the art, ablative etching can be accomplished using any known source, as long as the source emits radiation in the wavelength range of less than 400 nm and as long as ablative photodecomposition occurs. One suitable source of ultraviolet wavelength radiation is an ArF excimer laser providing a pulsed output at 193 nm. Such lasers are commercially available.

Ablation is the process by which ultraviolet radiation having wavelengths less than 400 nm is capable of decomposing certain materials by electronically exciting the constituent bonds of the material, followed by bond-breaking and the production of volatile fragment materials which evaporate or escape from the surface. These photochemical reactions are known to be particularly efficient for wavelengths less than 200 nm (i.e., vacuum ultraviolet radiation), although wavelengths up to 400 nm have been used in surgery and other applications. In ablative photodecomposition, the broken fragments of biological matter carry away kinetic energy, thus preventing the energy from generating heat in the substrate.

To etch an organic polymer or biological tissue by ablative photodecomposition, it is necessary that the radiation be absorbed by the medium even at low laser power. However, many materials do not absorb sufficient energy to ensure ablation at low fluence. One possible solution to this problem is to dope these materials with a substance that increases the absorption cross-section of the material. This solution is unacceptable in many applications because doping will contaminate the entire sample to the depth of the desired etch.

It would, therefore, be desirable to etch by ablative photodecomposition using low fluence lasers. In one aspect, this invention relates to a method of etching using a first and second lasers. This combination of ultraviolet laser wavelengths may be used for medical and dental purposes, and more particularly for etching or eroding biological organic material or polymer substrates. Material can be selectively removed without undue heating or damage to the areas surrounding the area struck by the radiation. The technique and apparatus by which the organic material is removed, or etched, is different than that of the prior art, and the geometry of the etching pattern is completely defined by the incident radiation.

Many prior art systems include a second visible laser to aid in aiming a non-visible cutting laser. U.S. Pat. No. 3,710,798 Bredemeier and U.S. Pat. No. 4,289,378 Remy et al. describe laser cutting systems using lasers at two distinct wavelengths. A first laser in the visible spectrum illuminates the target area and a second, cutting laser ablates away the organic material.

U.S. Pat. No. 4,408,602 to Nakajima describes a laser ablation system using three laser sources, the radiation from each source being a distinct wavelength. A first source emits a beam in the visible spectrum to aim the laser while the second and third beams are independent cutting sources. The first of these two cutting sources is a $CO_2$ laser with a wavelength in the infrared region. The second of the cutting lasers is a "YAG" laser which has a wavelength in the visible spectrum. Each of these lasers is effective on different types of tissue. The apparatus in this patent enables an operator to easily switch between lasers, depending on the tissue he is attempting to cut.

Koren, in his article entitled "$CO_2$ Laser Assisted UV Ablative Photoetching of Kapton Films," published Jul. 1984 in *Applied Physics Letters*, describes the use of an infrared laser source to etch a polymer. In this arrangement, a plasma is created by focusing a first portion of the infrared laser radiation on a tungsten rod, creating an extremely high temperature. The continuous spectrum of ultraviolet (UV) and vacuum ultraviolet (VUV)

radiation generated by the plasma is focused on the polymer target along with a second portion of the infrared laser radiation, etching the target. This etch technique is not acceptable in many situations since the infrared laser will tend to cause thermal damage to the material being etched. In addition, this technique could not be used where fiber optics conduct and focus the radiation since infrared radiation is almost impossible to conduct through known optical fibers, especially at the fluencies described. Where a substrate is ablated by a single laser, the depth of ablation is a function of the wavelength of the incident radiation, the incident power (fluence) of the laser, and the number and duration of the pulses. Therefore, the etch depth may be controlled by changing any of these variables. However, in many situations, the wavelength (i.e., type of laser) and incident power are fixed by the limitations of the available equipment. In order to accurately control the etch characteristics under these circumstances it would be advantageous to be able to enhance the etch characteristics of the laser, for example, by using a second, longer wavelength laser in time coherence with the etching laser.

SUMMARY OF THE INVENTION

When a laser pulse of a suitable wavelength irradiates a portion of certain substrates, it excites the surface molecules which, if sufficiently excited, will ablate. Those molecules which are not sufficiently excited to ablate undergo a change in their absorption characteristics which makes them susceptible to ablation by a longer wavelength laser pulse. In the method of the present invention a first laser at a short wavelength creates a transient change in the absorption characteristics of a substrate. This first laser is set at a fluence that is sufficient to change the absorption characteristics of surface molecules. A second laser, with a wavelength within the absorption spectrum of the excited surface molecules, is used simultaneously with or at a fixed time after the first laser to ablate the excited molecules.

More particularly, in the present invention, ablative photodecomposition (APD) is used to etch organic polymers and biological layers. The incident radiation is comprised of multiple wavelengths. A region of the sample to be etched is first irradiated with radiation in the absorption spectrum of the substrate (normally the ultraviolet range) and the region is thereafter (or simultaneously) irradiated with a second, longer wavelength pulse (which need not be in the ultraviolet range). Normally this second irradiation pulse will be within the absorption spectrum of the molecules excited by the first irradiation.

It is an object of the present invention to provide a means of enhancing the ablation characteristics of an ultraviolet laser.

It is a further object of the present invention to enhance the ablation characteristics of an ultraviolet laser using a second, longer wavelength laser in time coherence at a fixed time after the first ultraviolet laser pulse.

BRIEF DESCRIPTION OF THE DRAWINGS

The novel features of the invention are set forth with particularity in the appended claims. The invention itself, however, both as to organization and method of operation, together with further objects and advantages thereof, may best be understood by reference to the following description taken in conjunction with the accompanying drawings in which:

DETAILED DESCRIPTION OF THE PREFERRED EMBODIMENT

The use of two wavelengths enhances the etching efficiency by causing a transient change in the absorption characteristics of the sample. This aids in etching samples which are otherwise difficult to etch and enables the use of wavelengths whose absorption is typically minimal in these samples. For example, long wavelength ultraviolet radiation is easier to transmit optically (i.e., through the air or optical fibers), but organic polymers often have minimal absorption at these long wavelengths. By changing the sample's absorption characteristics, the long wavelength radiation can be used and will cause etching. Further, while short wavelength ultraviolet radiation has high absorption in most organic materials, such short wavelengths are difficult to transmit through optical fibers. When multiple wavelengths are used, the energy fluence of the short wavelength radiation can be minimized to prevent fiber optic damage without sacrificing etching efficiency.

Figure 1:
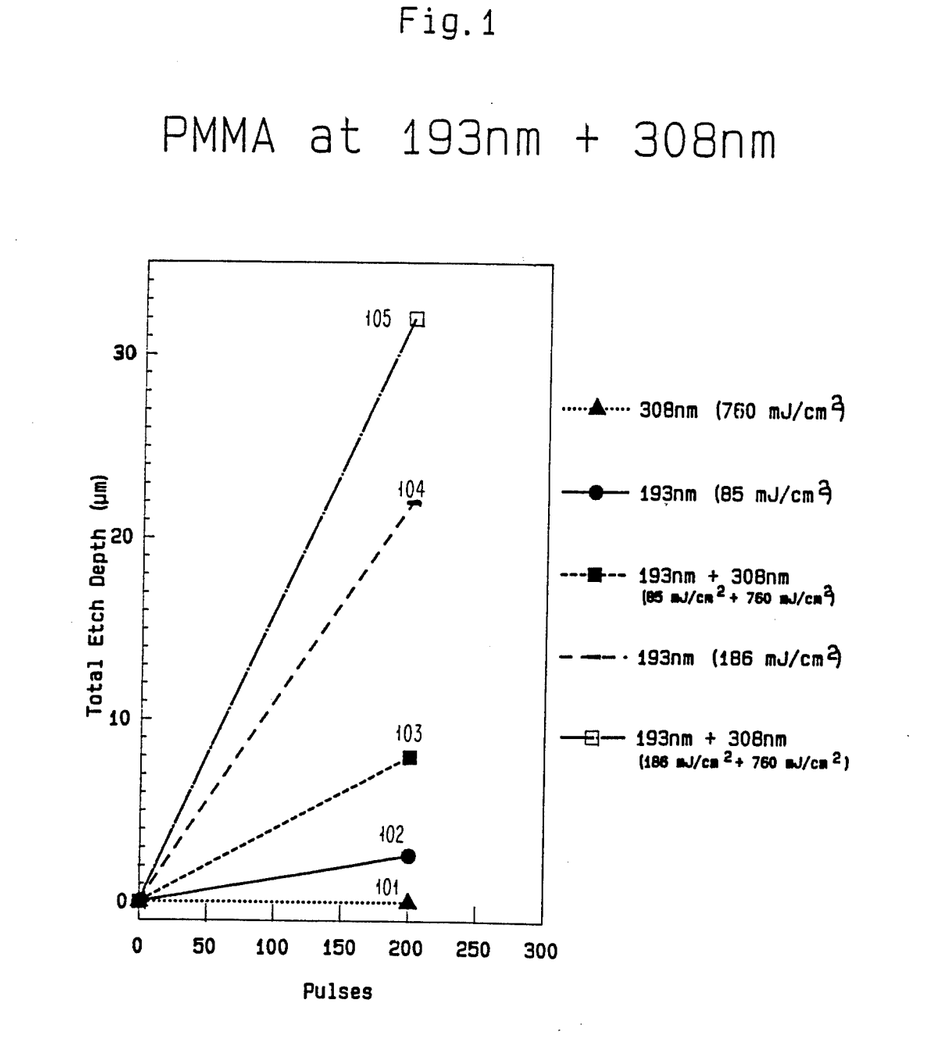
FIG. 1 is a plot of etch depth as a function of the number of pulses for a number of wavelengths and power settings using a PMMA substrate.

FIG. 1 is a graph of etch depth vs. number of pulses for five combinations of laser power using a poly(-methyl methacrylate) (PMMA) substrate. Plot 101 is the etch depth per pulse of a 308 nm XeCl pulsed excimer laser at a fluence of 760 mJ/cm$^2$ (milliJoules per square centimeter). Plot 102 is the etch depth per pulse of a 193 nm ArF pulsed excimer laser at a fluence of 85 mJ/cm$^2$. Plot 103 is the etch depth per pulse of the time coincident combination of a 193 nm laser at a fluence of 85 mJ/cm$^2$ and a 308 nm laser at a fluence of 760 mJ/cm$^2$. Plot 104 is the etch depth per pulse of a 193 nm laser at a fluence of 186 mJ/cm$^2$. Plot 105 is the etch depth per pulse of the time coincident combination of a 193 nm laser at a fluence of 186 mJ/cm$^2$ and a 308 nm laser at a fluence of 760 mJ/cm$^2$. PMMA does not absorb very much 308 nm radiation. To etch PMMA with laser pulses at this wavelength, a thermal mechanism must be used. This thermal mechanism requires high fluences (greater than 1 J/cm$^2$) and high repetition rates (greater than 20 Hz) which cause intense local heating and result in considerable thermal damage to the etched substrate.

In contrast, smooth etching can be obtained using coincident pulses of 193 nm and 308 nm radiation. Plot 101 of FIG. 1 illustrates that, at a fluence of 760 mJ/cm$^2$ of 308 nm radiation, the PMMA substrate was not etched to any measurable extent. FIG. 1 also illustrates that etching was achieved using 193 nm radiation at fluences of 85 and 186 mJ/cm$^2$. However, the combination of the two wavelengths resulted in a 30 to 100 percent increase in the etch depth per pulse pair. In addition, the etched area had a smoothness (i.e., no thermal damage) that is typical of laser etching with 193 nm laser pulses alone. Similar results were obtained on animal tissue (in vitro) using the same two wavelengths. There is every expectation that these results can be improved upon by inserting a time delay between the two pulses. Further, it would also be expected that it would be advantageous to follow the 193 nm pulse with the 308 nm pulse.

Figure 2:
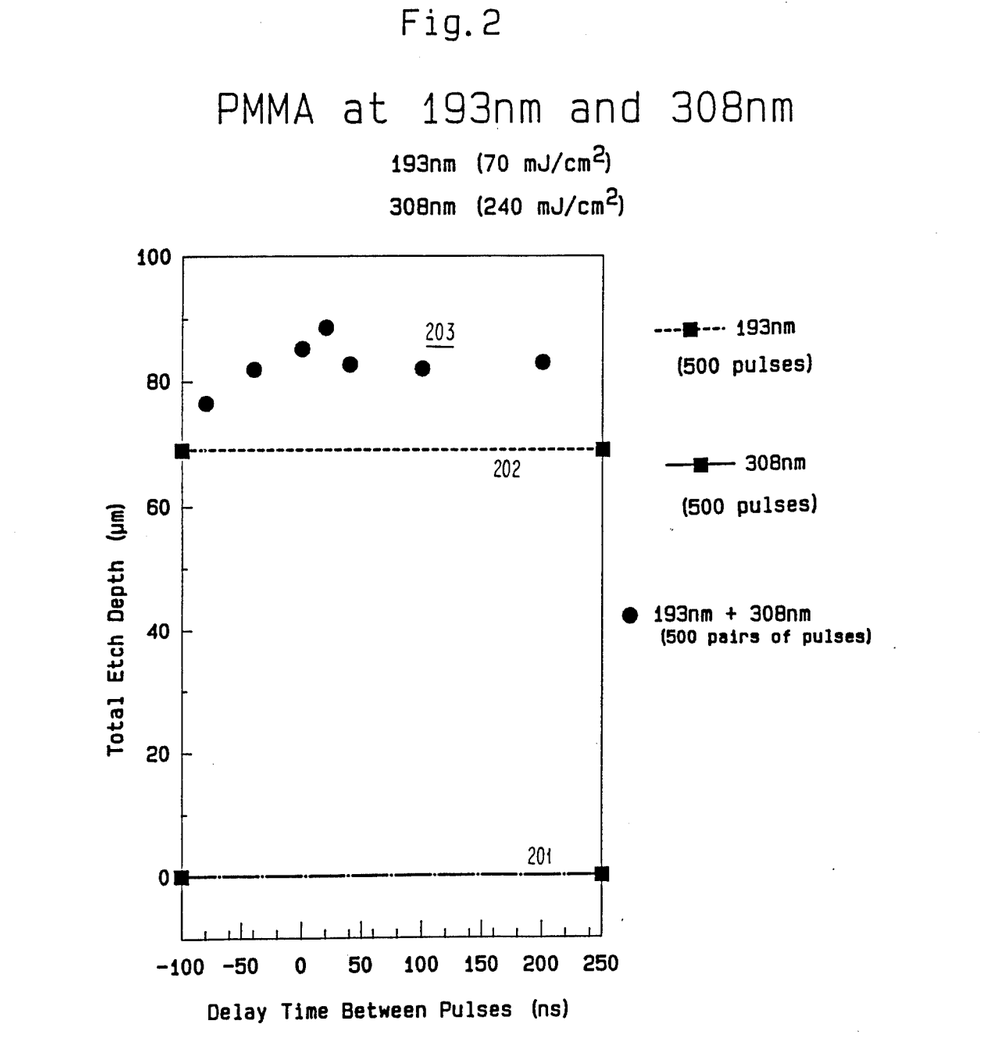
FIG. 2 is a plot of etch depth after 500 pulses as a function of the delay time between pulses using a PMMA substrate.

FIG. 2 illustrates an experiment conducted on PMMA to determine the effect of inserting a time delay between the 193 nm ArF laser pulses and 308 nm XeCl laser pulses. The 193 nm laser was set at a fluence of 70 mJ/cm$^2$. The 308 nm laser was set at a fluence of 240 mJ/cm$^2$. As plot 201 illustrates, the 308 nm, longer wavelength laser had no measurable effect on the substrate when used alone, which would be expected because the wavelength of the 308 nm laser is outside the absorption spectrum of PMMA. The 193 nm laser, in contrast, is well within the absorption spectrum of PMMA and etched the PMMA to a depth of approximately 70 micrometers after 500 pulses (plot 202).

Plot 203 in FIG. 2 clearly illustrates that the combination of the 193 nm laser and the 308 nm laser provided a substantial improvement in etch depth per pulse pair, and that the degree of improvement depended on the temporal relation between pulses at the two wavelengths. In addition, when the 308 nm laser pulse preceded the 193 nm laser pulse, the effect was not as substantial as when the 193 nm pulse preceded the 308 nm pulse. As can be seen from plot 203, this improvement peaked when the 308 nm pulse followed the 193 nm pulse by approximately 20 to 30 nanoseconds. Of course, different laser wavelengths will have different optimum time separations. For example, the peak in plot 203 would be expected to occur at approximately 40 to 50 nanoseconds of separation using a 248 nm KrF pulsed excimer laser in place of the 193 nm laser. Therefore, the combined effect of the two lasers provides a substantial improvement over using either laser alone, and an even further improvement is provided when the lasers are used in a specific time sequence.

It is expected that this time sequence, i.e., the optimum length of time between pulses, would be dependent on the type of substrate being ablated, the maximum ablation occurring at different time spacings for different substrates. However, it would also be expected that the shorter wavelength, higher photon energy laser pulse should come first in every instance, with the longer wavelength, lower photon energy (not necessarily lower incident energy) laser pulse being applied second.

The timing of the peak illustrated in FIG. 2 is expected to be independent of the laser power. That is, while the height of the peak will be a function of the incident power, the optimum pulse separation time is not expected to be a function of the incident power. Therefore, the etch depth per pulse may be controlled as a function of the time separation between the two laser pulses for a fixed incident power. In addition, by controlling the pulse separation time it is possible to achieve desirable etch depths with lower incident power levels.

It has been speculated that the improved etch results from the following physical phenomenon: as with ablation, the surface molecules of the substrate are excited to a higher electronic state by a UV laser with a wavelength within the absorption spectrum of the substrate material. The excited molecules have an absorption spectrum which includes the longer wavelength laser, and, therefore, will absorb the energy from the second laser where the unexcited substrate does not absorb energy from the second laser. This phenomenon results in ablation of the excited molecules which were not ablated using the single UV laser.

According to this theory, when a molecule is excited to a higher energy state such as a "singlet", it may not reach an energy level sufficient to break the molecular bonds and ablate. When this happens, the singlet molecules form "triplets", which is also an excited state. If no additional energy is added, the triplets will simply reform as surface molecules. However, a second laser with a wavelength within the absorption spectrum of the excited triplets can add sufficient energy to cause the bonds to be broken and ablation to occur. This additional energy will not be necessary to cause ablation of a substantial majority of the molecules where the shorter wavelength laser provides sufficient energy for the bonds to be broken and ablation to occur. However, it will be necessary in some percentage of the cases where the shorter wavelength laser does not provide sufficient energy for ablation. The improvement in etch depth may then be explained by the additional molecules ablated by the second laser.

More specifically, with a PMMA substrate, 193 nm radiation is used first because that wavelength is within the absorption spectrum of PMMA and excites the substrate molecules sufficiently to cause them to ablate. When the 193 nm radiation strikes the substrate, the photon energy is sufficient to excite a number of the surface molecules into a "singlet" state. A majority of the molecules in the singlet state have sufficient energy to ablate. However, some of the molecules do not ablate and slide into a triplet state. Molecules in the triplet state can be excited into ablation provided that radiation with sufficient photon energy—in the case of PMMA, a 308 nm laser—is incident on the substrate at that point. The 308 nm radiation, being within the absorption spectrum of the triplet molecules, provides sufficient energy to excite the "triplets" into ablation, resulting in substantially improved etch depths. Thus, the wavelength of a first laser is selected to be within the absorption band of the substrate in order to sufficiently excite the substrate molecules. The wavelength of a second laser is selected to be within the absorption spectrum of the excited triplet molecules. Normally a second laser with a longer (that is, less powerful—having lower photon energy) wavelength is required, which excites into ablation those molecules not removed by the first laser into ablation, and essentially "cleans" the hole.

This is the best explanation known to the inventors for the advantageous effects of the present invention which might also possibly be explained by a free radical theory. However, a free radical theory would not be expected to result in the sharp peaking seen in FIGS. 1 and 2. Further, it is not believed that the heat theories relied upon to explain infrared etching are applicable to the present invention. Because the substrates being etched are insulators (e.g., polymers), if heat were the cutting mechanism, irradiation by two lasers would be expected to result in a peak etch at zero pulse separation time and increasing time separation would not be expected to result in the sharp drop-off in etch depth illustrated in FIGS. 2 and 3. A steep drop-off would not be expected because the rate of dissipation of heat in such insulators is much slower than the drop-off illustrated.

Referring back to the Koren article discussed previously, that apparatus etched by lowering the ablation threshold of the substrate, which ensured that the fluence of the broad-spectrum UV and VUV plasma radiation would be sufficient to cause etching. In Koren, the author describes an etch mechanism wherein a broad spectrum (from visible to UV to VUV) of plasma generated ultraviolet radiation is focused on a particular spot to produce a fluence of approximately 1.5 J/cm$^2$. A second beam of scattered infrared radiation is simultaneously focused on the same spot at a fluence of approximately 23 J/cm$^2$, and the combined thermal effect of the infrared laser radiation and the photochemical (ablative) effect of the broad-spectrum plasma generated radiation etches the substrate. As the author explains, the etch mechanism is a combination of the photochemical effect of the UV photons, which causes bond breaking in a thin layer close to the film's surface, and the thermal effect of the infrared photons, which are absorbed by the UV-sensitized layer allowing ablation. The role of the infrared photons is to raise the temperature of the film, which lowers the threshold fluence of UV radiation required to induce photoablative decomposition. It has been previously shown that raising the temperature of a Kapton (trademark of the Du Pont Corporation) polyimide substrate will, under certain circumstances, lower the fluence threshold for ablative etching. Although this technique is useful in etching substrates such as Kapton (trademark of the Du Pont Corporation), which has a high absorption coefficient, and it may be useful in etching other materials and in certain surgical procedures, its usefulness is limited by the heat generated. In addition, its usefulness is further limited by the difficulty of transporting infrared radiation using fiber optics and by the equipment required to generate broad-spectrum plasma radiation. In contrast, the present invention uses a purely photochemical etch mechanism which does not generate detrimental heat within the material being etched.

Another advantage of the present invention is that it makes use of an ablation technique adaptable to the optical fiber environment. Normally, the ultraviolet lasers which give the best ablation (in FIG. 1 the 193 nm far-UV laser), tend to damage or destroy optical fiber when used at incident power levels which are sufficient for etching. However, longer wavelength lasers (e.g., the 308 nm laser) may be used at substantially higher power levels without destroying the fiber optics. Thus, by combining two laser wavelengths, it is possible to etch efficiently in situations where it would not have been possible to effectively etch the substrate using either laser independently. That is, while simply increasing the incident energy fluence of the 193 nm laser would result in a deeper etch depth per pulse, it is not always possible or desirable to simply increase the incident power. Increasing the energy fluence will, for example, while maintaining an acceptably larger etch area, exceed the power output of most commercially available lasers. Further, at higher energy fluence levels a 193 nm UV laser approaches the theoretical limits of the optical fiber to carry radiation. Therefore, it is necessary to find an alternative which increases the etch depth per pulse without increasing the energy fluence of the 193 nm laser.

Figure 3:
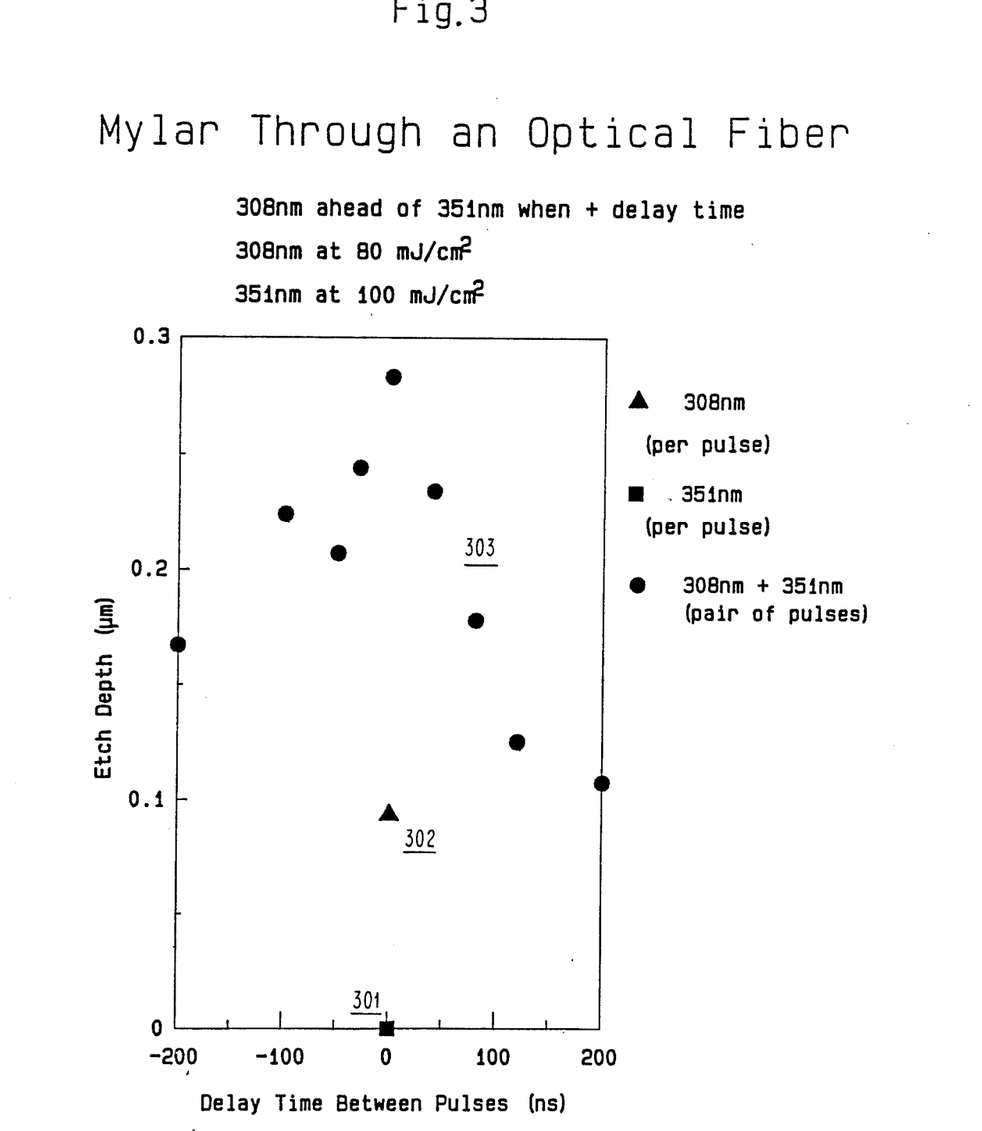
FIG. 3 is a plot of etch depth per pulse or pair of pulses as a function of the delay time between pulses using a mylar substrate and an optical fiber system to carry the laser beam.

FIG. 3 illustrates results of an application of the present invention to the ablation of a mylar-type substrate. In this experiment the lasers were conducted through optical fibers. The first laser utilized was a 308 nm XeCl pulsed excimer laser at an energy fluence of 80 mJ/cm$^2$, which is within the absorption spectrum of mylar. The second laser was a 351 nm XeF pulsed excimer laser at an energy fluence of 100 mJ/cm$^2$, which is outside the absorption spectrum of unexcited mylar. The 351 nm laser did not have a measurable effect on the mylar when used alone (see plot 301), however, one pulse of the 308 nm laser did etch the mylar to an average depth of approximately 0.14 micrometer per pulse (see plot 302) However, when the effects of the 308 nm and the 351 nm lasers were combined, the improvement in etch depth was substantial. Plot 303 of FIG. 3 illustrates the average etch depth per pulse pair obtained by separating the first and second laser pulses in time. It will be noted that the optimum delay time between pulses in FIG. 3 is substantially less than the optimum delay time in FIG. 2, which substantiates the expectation that the optimum delay time will vary depending on the substrate material and/or the frequency of the incident radiation.

In FIGS. 2 and 3, in the time period of less than 0 (i.e., where the longer wavelength laser pulse was followed by the shorter wavelength laser pulse), the etch characteristics were also improved over either laser alone. One possible explanation for this phenomenon is that the tail end of the long wavelength laser pulse overlapped the rising portion of the short wavelength laser pulse sufficiently to enhance the effect of the short wavelength laser pulse. However, this would not be a preferred arrangement.

Figure 4:
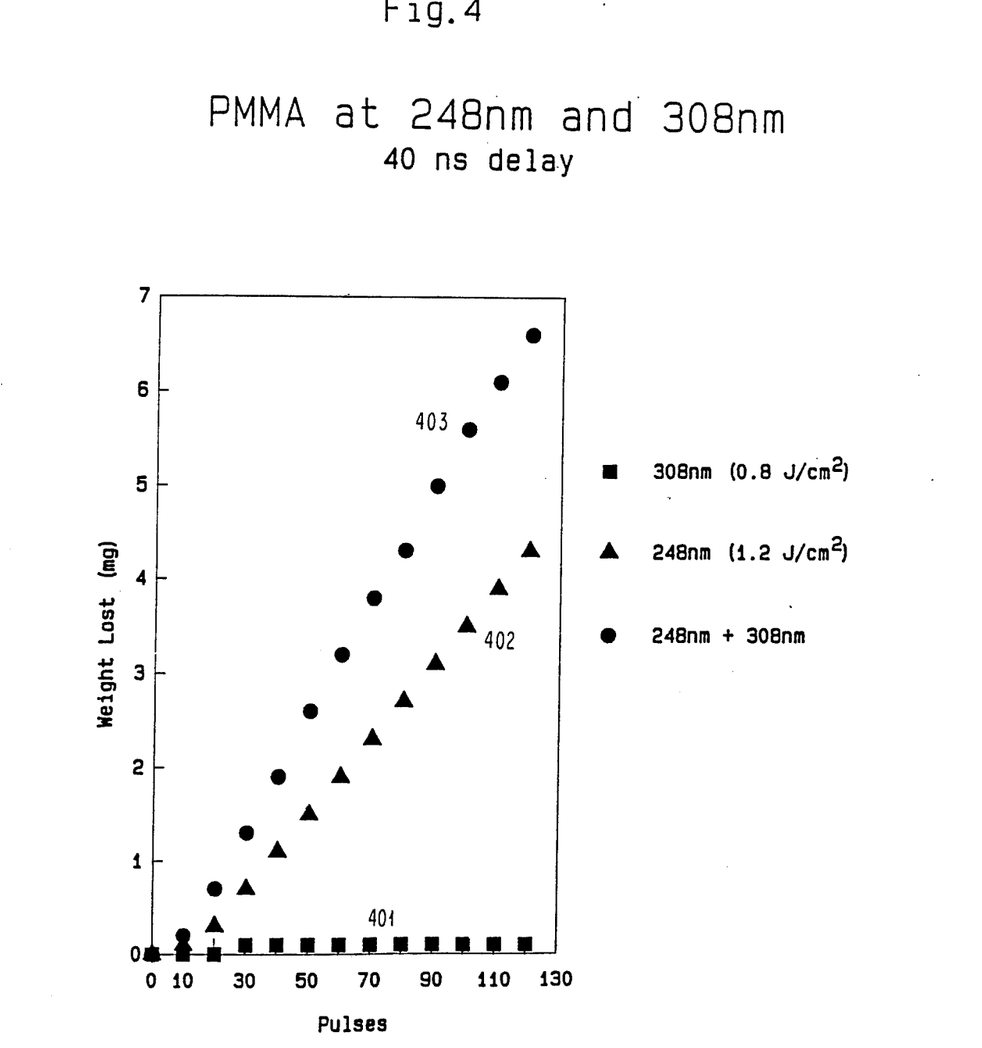
FIG. 4 is a plot of the weight lost as a function of the number of pulses using a PMMA substrate.

FIG. 4 illustrates the weight loss in milligrams as a function of the number of pulses for a PMMA substrate. Plot 401 illustrates the loss as a function of the number of pulse pairs using a 308 nm laser at a fluence of 800 mJ/cm$^2$. The weight loss indicated in plot 401 of FIG. 4 at 308 nm was not a result of etching. It may have been caused by measurement error or by the release of surface gases; however, there was no visible evidence that any etching had taken place. Plot 402 illustrates the weight loss as a function of the number of pulse pairs using a 248 nm laser at a fluence of 1.2 J/cm$^2$. Finally, plot 403 illustrates the weight loss as a function of the number of pulse pairs using a 248 nm laser at a fluence of 1.2 J/cm$^2$ followed by a 308 nm laser at a fluence of 800 mJ/cm$^2$ with a 40 nanosecond delay between the 248 nm and 308 nm pulses.

Figure 5:
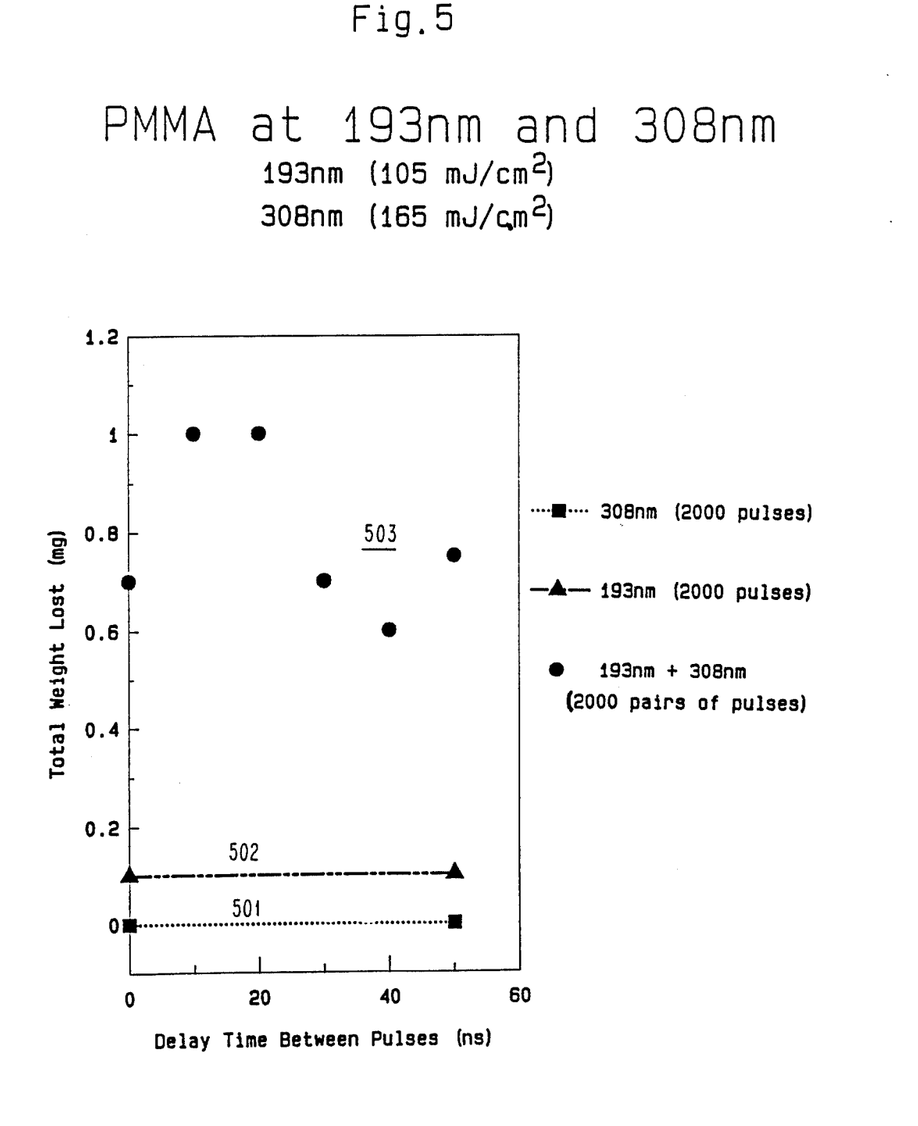
FIG. 5 is a plot of the total weight lost after 2000 pulses as a function of the delay time between pulses using a PMMA substrate.

FIG. 5 is a plot of the weight loss in milligrams vs. the time delay between pulses for a PMMA substrate. The lasers are a 193 nm laser at a fluence of 105 mJ/cm$^2$ and a 308 nm laser at a fluence of 165 mJ/cm$^2$. Plot 501 illustrates that there was no measurable weight loss after 2000 pulses of the 308 nm laser alone. Plot 502 illustrates that there was only about 0.1 mg loss after 2000 pulses of the 193 nm laser. Plot 503 illustrates that there was a substantial improvement when the 193 nm laser and 308 nm laser were used with a predetermined time delay. Comparing this figure to FIG. 2, it is clear that the peak improvement occurs at substantially the same time, i.e., at approximately 10-20 nanoseconds of delay.

Figure 6:
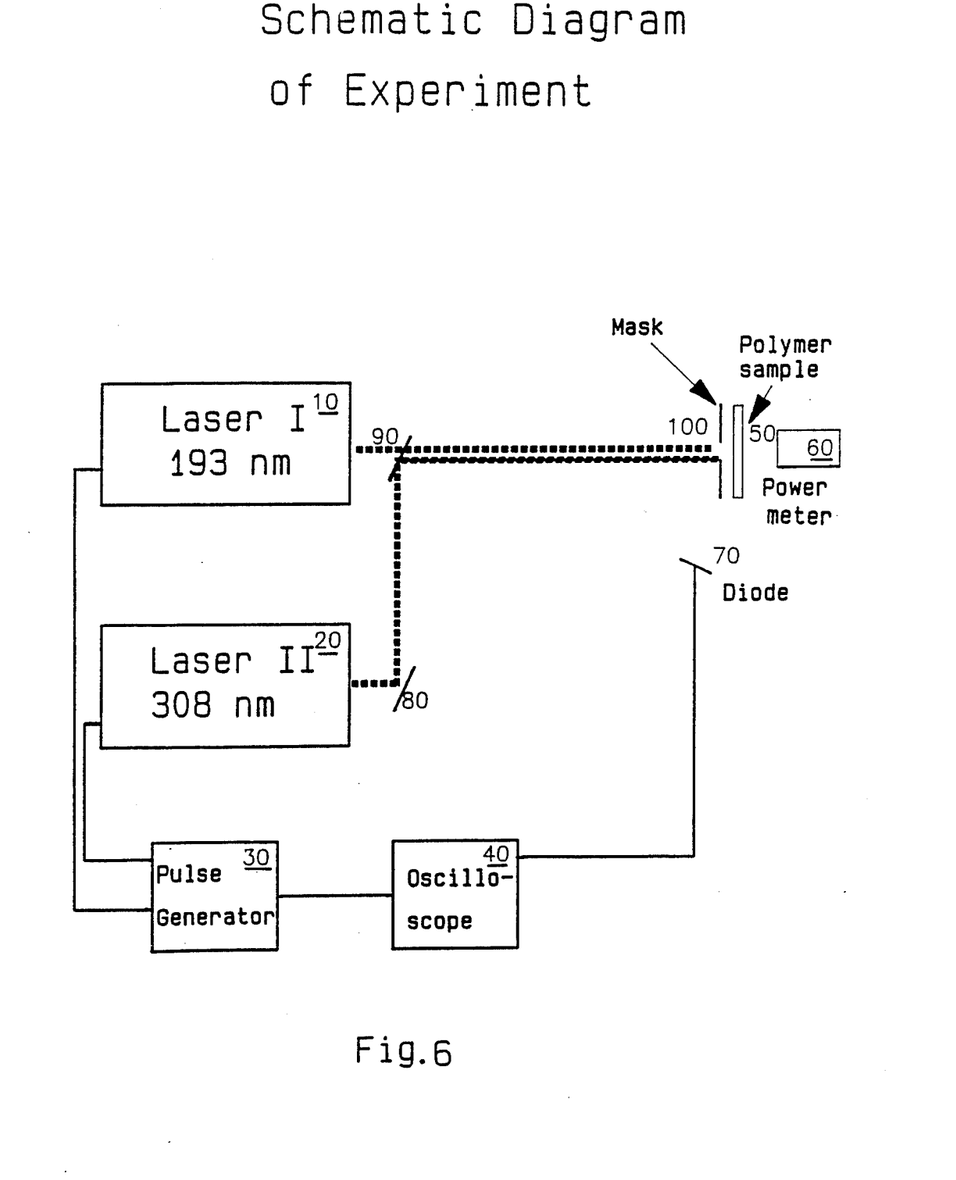
FIG. 6 illustrates an arrangement which may be used to implement the present invention.

FIG. 6 illustrates an arrangement for implementing the present invention. In FIG. 6, a first Lambda-Physik 201E ArF pulsed excimer UV laser 10 produces a pulse of 193 nm wavelength when triggered by a first pulse from a Philips PM 5716 pulse generator 30 which is capable of generating a second pulse at a fixed time delay after the first pulse. The second pulse triggers a Lambda-Physik 201E XeCl pulsed excimer laser 20 which provides a 308 nm pulsed beam that is reflected from both a first mirror 80 and a second, dielectric mirror 90. Mirror 90 is arranged to pass radiation from the 193 nm laser with little or no loss. Radiation from the two lasers is focused on a sample which might be PMMA or other type of substrate. Mask 100 limits the region of sample 100 which may be irradiated. Silicon Photodiode 70 and Textronix model 2467 oscilloscope 40 may be used to determine the shape and time separation of the first and second pulses. Photodiode 70 absorbs a portion of the radiation from lasers 10 and 20, and its output is displayed on oscilloscope 40 which is triggered by an output from pulse generator 30. A Scientech 38-2UV5 powermeter measured the power through the mask (without the polymer).

In short, shorter UV wavelengths (e.g., 193 nm) cannot normally be transmitted through conventional fiber optics without substantial losses. At power levels sufficient to make the UV laser alone efficient, these losses may result in damage to the optical fiber. Using the present invention, very short wavelength ultraviolet laser radiation, which is difficult to produce and deliver at high energy fluence, can be used at lower fluence with an additional, longer wavelength laser to achieve desirable etch characteristics. The cost of using two lasers is not prohibitive because the power supply and delivery systems can be shared by the two lasers. This makes the present invention especially appealing for laser angioplasty.

The method described in the present invention is intended to be applicable to any type of substrate which may be etched by ablative photodecomposition. It is particularly adapted to etching organic substrates such as organic polymers, organic tissue, bone and tooth material. While preferred embodiments of the present invention have been shown and described herein, it will be obvious to those skilled in the art that such embodiments are provided by way of example only. Numerous variations, changes, and substitutions will now occur to those skilled in the art without departing from the invention. For example, the concept of this invention can also be extended to the APD of any material (such as an oxide, etc.) that can be photochemically ablated. Accordingly, it is intended that the invention be limited only by the spirit and scope of the appended claims.

We claim:

1. A method of ablating a portion of a substrate, comprising the steps of:
   exposing said substrate to a first radiation pulse at a first ultraviolet wavelength; and
   exposing said substrate to a second radiation pulse at a second, longer ultraviolet wavelength, at least one of said first or second radiation pulses being of sufficient energy fluence to exceed the threshold for ablative photodecomposition of said substrate.
2. The method of claim 1 wherein:
   said first and second radiation pulses are substantially simultaneous in time.
3. The method of claim 1 wherein:
   said first radiation pulse irradiates said substrate prior to said second radiation pulse.
4. The method of claim 3 wherein:
   said first radiation pulse precedes said second radiation pulse by a predetermined time interval.
5. The method of claim 4 wherein:
   said predetermined time interval is selected to maximize the etch depth per pair of said first and second radiation pulses.
6. The method of claim 1 wherein:
   said one of said first and second radiation pulses is said second pulse.
7. The method of claim 6 wherein:
   said first and second pulses are substantially simultaneous in time.
8. The method of claim 6 wherein:
   said first radiation pulse precedes said second radiation pulse by a predetermined time interval.
9. The method of claim 8 wherein:
   said predetermined time interval is selected to maximize the etch depth per pair of said first and second radiation pulses.
10. The method of any of the preceding claims wherein:
    said substrate is an organic material.
11. The method of any of claims 1–9 wherein:
    said ultraviolet wavelengths are defined as wavelengths between 150 nm and 400 nm.
12. The method of any of claims 1–9 wherein:
    said steps are repeated a predetermined number of times.
13. A method of etching a portion of a substrate, comprising the steps of:
    irradiating said portion of said substrate with a first pulse of ultraviolet radiation for a time sufficient to cause a transient change in the absorption characteristics of said portion of said substrate; and
    irradiating said portion of said substrate with a second pulse of longer wavelength ultraviolet radiation with sufficient energy fluence to cause ablative photodecomposition of said portion of said substrate.
14. The method of claim 13 wherein:
    said irradiating steps are repeated a predetermined number of times.
15. The method of claim 13 wherein:
    said irradiating steps occur simultaneously.
16. The method of claim 13 wherein:
    said first pulse precedes said second pulse.
17. The method of claim 16 wherein:
    said first pulse precedes said second pulse by a predetermined interval of time.
18. The method of claim 17 wherein:
    said predetermined interval of time is selected to optimize the etch depth per pair of said first and second pulses.
19. The method of claim 13 wherein:
    said substrate is an organic polymer.
20. A method of ablatively photodecomposing polymers and biological layers without substantial thermal effects wherein:
    photodecomposition is accomplished by irradiating said layers with multiple wavelength radiation of sufficient energy fluence to exceed the threshold of ablative photodecomposition of said layers, at least one of said wavelengths being in the ultraviolet range.
21. The method of claim 20 wherein:
    said radiation comprises laser pulses of distinct wavelengths; and
    said laser pulses are spacially coincident.
22. The method of claim 21 wherein:

said laser pulses are spaced in time, a pulse of said one wavelength radiation in the ultraviolet range preceding a pulse of second wavelength radiation by a predetermined period.

23. The method of claim 22 wherein:
said pulse of second wavelength radiation is within the ultraviolet range.

24. A method of etching a portion of a substrate, comprising the steps of:
irradiating said portion of said substrate with a first radiation pulse whose wavelength is within the absorption spectrum of said substrate;
irradiating said portion of said substrate with a second, longer wavelength radiation pulse at a predetermined time after irradiating the substrate with said first radiation pulse;
at least one of said pulses having sufficient energy fluence to exceed the threshold for ablative photodecomposition of said substrate.

25. The method of claim 24 wherein:
said wavelength of said second, longer wavelength radiation pulse is within the absorption spectrum of molecules of said substrate excited by irradiating said portion with said first radiation pulse.

26. The method of claim 24 wherein:
said first and second radiation pulses are laser pulses; and
each said first pulse is followed at said predetermined time by said second pulse.

27. The method of claim 26 wherein:
irradiation of said substrate by said first and second laser pulses continues for a predetermined number of pulses.

28. A method of etching a portion of a substrate, comprising the steps of:
irradiating said substrate with a first light pulse of sufficient photon energy to cause surface molecules of said substrate to be converted to a singlet state, said photon energy of said first light source being further sufficient to photochemically ablate at least some of said molecules raised to said singlet state; and
irradiating said substrate with a second light pulse having sufficient photon energy to cause a portion of said molecules not photochemically ablated by said first light source to absorb sufficient energy to photochemically ablate.

29. An apparatus for enhancing ablation of a portion of a substrate comprising:
a first radiation source for generating radiation of a first wavelength;
a second radiation source for generating radiation of a second longer wavelength;
means for directing radiation from said first and second radiation sources to substantially the same area of said substrate;
means associated with said first and second radiation sources for controlling the time separation between generation of radiation by said first and second radiation sources.

30. The apparatus of claim 29 wherein:
said radiation of said second wavelength is of sufficient energy fluence to cause ablative photodecomposition of said substrate area when said area is irradiated by said radiation of said first wavelength.

* * * * *